United States Patent
Wu et al.

(10) Patent No.: US 6,853,742 B2
(45) Date of Patent: Feb. 8, 2005

(54) APPARATUS AND METHOD FOR CHARACTERIZING FIBER CRIMPS

(75) Inventors: Yejia Wu, Midlothian, VA (US); Nicholas Leoncavallo, Jr., Irmo, SC (US); Thomas Yiu-Tai Tam, Richmond, VA (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 10/716,572

(22) Filed: Nov. 18, 2003

(65) Prior Publication Data

US 2004/0156534 A1 Aug. 12, 2004

Related U.S. Application Data

(63) Continuation of application No. 09/621,845, filed on Jul. 24, 2000, now Pat. No. 6,674,887.

(51) Int. Cl.[7] .............................................. G06K 9/00
(52) U.S. Cl. ........................................ 382/141; 348/86
(58) Field of Search ................................. 382/141, 145, 382/152, 173, 174, 181, 206, 225, 268, 269, 273, 274, 309; 348/86, 88, 92, 447, 448; 358/501, 504

(56) References Cited

U.S. PATENT DOCUMENTS

| 4,232,336 A | 11/1980 | Henry .......................... 358/106 |
| 4,240,110 A | 12/1980 | Henry .......................... 358/107 |
| 4,274,746 A * | 6/1981 | Cardell et al. ............... 356/429 |
| 4,415,926 A | 11/1983 | Henry .......................... 358/107 |
| 4,737,846 A | 4/1988 | Tokuno et al. ............... 358/106 |
| 5,351,308 A | 9/1994 | Kaminer et al. ................ 382/8 |
| 6,043,840 A * | 3/2000 | Wu et al. ....................... 348/88 |
| 6,340,992 B1 * | 1/2002 | Markandey .................. 348/556 |
| 6,392,712 B1 * | 5/2002 | Gryskiewicz et al. ........ 348/584 |

FOREIGN PATENT DOCUMENTS

| EP | 0459826 | * 4/1991 | ............ D02G/1/12 |
| WO | WO97/40341 | * 10/1997 | ........... G01B/11/30 |

* cited by examiner

*Primary Examiner*—Daniel Miriam
(74) *Attorney, Agent, or Firm*—Bingham McCutchen LLP; Sandra P. Thompson

(57) ABSTRACT

Apparatus and method are described for measuring and controlling the crimp characteristics of a moving crimped tow. A light source illuminates a section of the moving crimped tow and at least one progressive scanning camera acquires a non-interlaced video image of the tow. The acquired image is digitized and a processor analyzes the non-interlaced image. Crimp characteristics are derived based on this analysis.

17 Claims, 21 Drawing Sheets

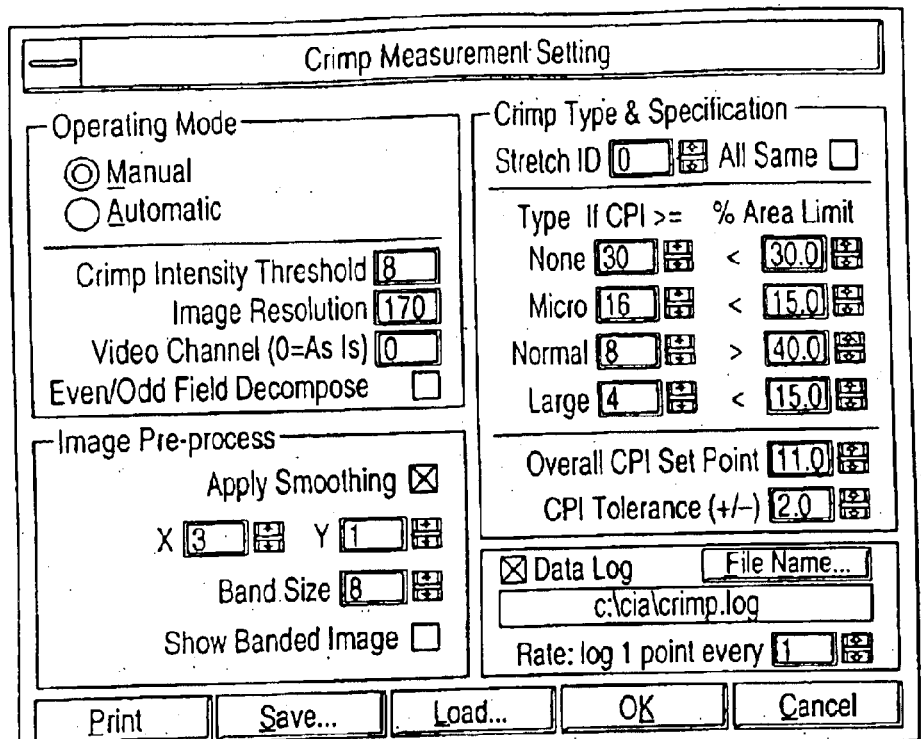
Measurement Setting For Manual Mode   FIG. 6A
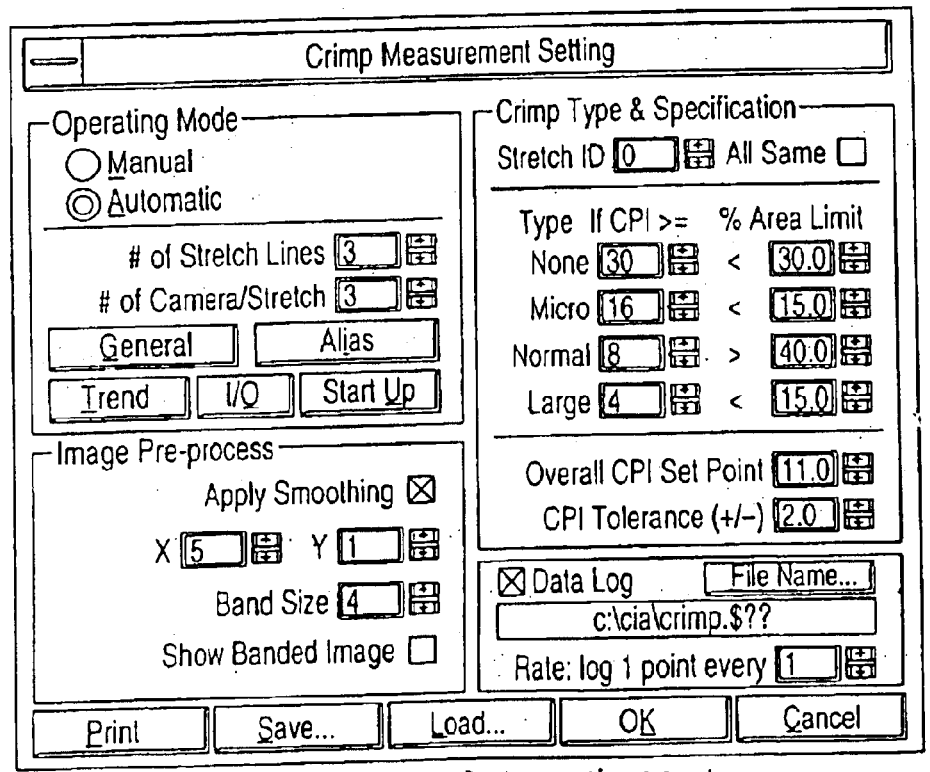
Measurement Setting For Automatic Mode   FIG. 6B 'General' for Automatic Mode

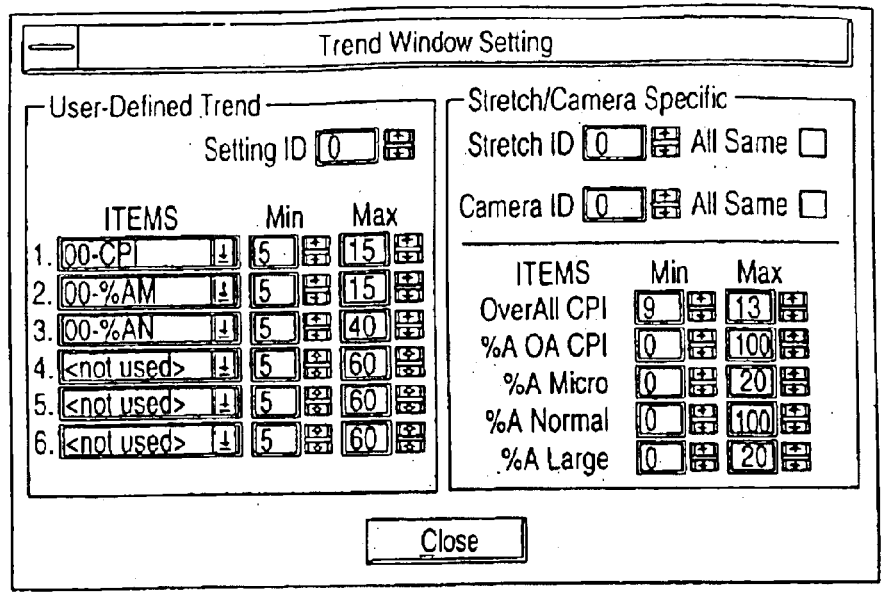
'Trend' for Automatic Mode  FIG. 7C
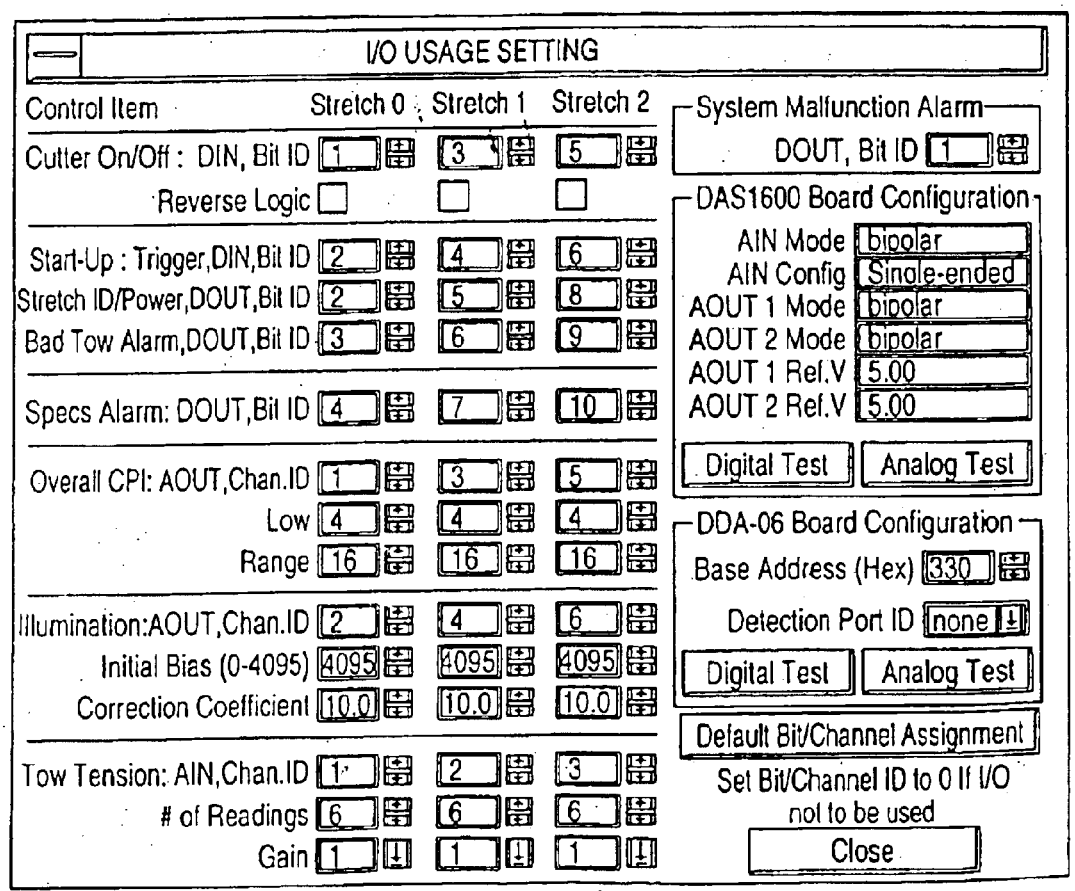
'I/O' for Automatic Mode  FIG. 7D 'Start Up' for Automatic Mode Main Control Panel And Measurement Results Of The Current Image Trend Window of Moving Average Alarm/Event Message Window 'Digital Test' for I/O Usage Setting 'Analog Test' for
I/O Usage Setting

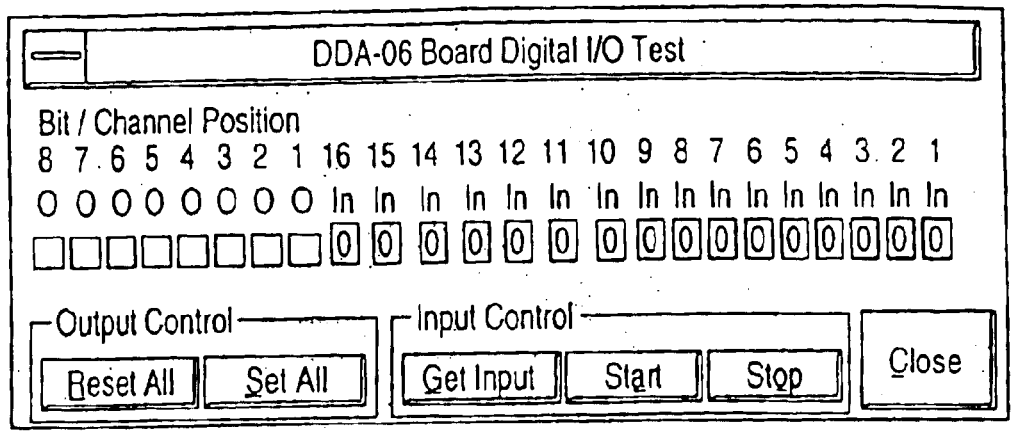
'Digital Test' for I/O Usage Setting    FIG. 11C
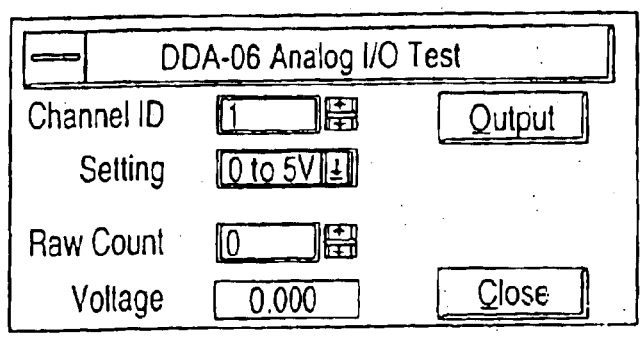
'Analog Test' for
I/O Usage Setting
FIG. 11D

FIG. 12A

```
/*----------------------------------------------------------------
Measurement function activated by system's timer
----------------------------------------------------------------*/
static void PNEAR NormalMeasurement(HWND hwnd)
{
    HANDLE hDIB[2];                          // handle to newly captured images
    LPIOUSAGE lpIO;                          // pt to IO setting data
    int err=0, maCalc[2]=(0,0);              // flag for error and moving avg calculation status
    int s,c,idxm,idxm2,i,k;                  // loop control variables
    float oaCPI[2];                          // avg overall cpi of a stretch
    int nCPI[2];                             // # of images for avg overall cpi calculation
    float avgIntensity;                      // avg image intensity of a stretch
    int nIntensity;                          // # of images for avg image intensity calculation
    extern LONG nUntitled;                   // # of image windows created since system started idxm=lpRes->IdxM+1;
    for(s=0; s<lpCFG->nStretch; s++) {       // get moving avg buffer idx
        lpIO=&lpCFG->Io[s];                  // loop over 3 stretchers, actual # can be varied by user
        if(lpIO->suTrig>=0 && ioIsStartup(lpIO->suTrig,s)) { // get pt to io setting data
            StartUpMode(hwnd,suENTER); return; // check start-up mode trigger oaCPI[0]=oaCPI[1]=0.0f; nCPI[0]=nCPI[1]=0;    // init. variables of avg overall CPI
        avgIntensity=0.0f; nIntensity=0;              // init. variables of avg image intensity
        for(c=0; c<lpCFG->nCamera; c++) {             // loop over 3 cameras, actual # can be varied by user
            hDIB[0]=hDIB[1]=NULL;                     // initialize memory handle to NULL
            if(!lpCFG->disableCamera[s][c] &&         // camera not disabled
               (lpIO->cutter<0 ||                     // cutter I/O not used
                ioIsCutterOn(lpIO,s))) {              // or cutter is ON
                if(err=GetLiveImage(lpCFG->actype[s].dpi,hDIB)) goto EXIT;
                if(lpIO->tension>=0) ioGetTowTension(lpIO);
                ...
            }
            if(lpCtl->LastVideoCode!='2') {           // switch video channel if more than 1 camera used
                                                      // advance to next channel
            }
            for(i=0;i<nImgCap;i++) {                  // loop over 2 field-decomposed images
                if(hDIB[i]) {                         // image captured with GetLiveImage()
                    wsprintf(lpCtl->LogName, cMg(73),s,c,cMg(39+i),nUntitled+1);
                    if(!ImageWindowAdd(hDIB[i],lpCtl->LogName,1)) { // create new image window
                        hDIB[i]=NULL; err=IDE_NoMemory; goto EXIT;   // fail to create new window
                    }
                    if(err=MeasureCrimpAuto(hwnd,s,c)) goto EXIT;    // measure crimp
                    if(MovingAvgGet(s,c,idxm2) {                     // calculate moving avg
```

FIG. 12B

```
            maCalc[i]++;
            oaCPI[i]+=lpMov[s][c]->pM[0][idxm2]; nCPI[i]++;    // cumulate if moving average calculated avgIntensity+=lpRes->avgIntensity;   // cumulate average image intensity for illumination control
        nIntensity++;
        }
        //--- end of loop over 2 images per capture
        // check user interrupts from mouse or keyboard
        //--- end of loop over cameras
    if(lpIO->illumin>=0 && nIntensity)  {             // check illumination if I/O enabled
        avgIntensity/=(float)nIntensity;
        if(avgIntensity>=(float)lpCFG->LowInt[s])  ioLightingNormal(lpIO,s,avgIntensity);
        ...
        }
    if(lpIO->oaCPI>=0)                                // output overall avg CPI
        for(i=0;i<nImgCap;i++) if(nCPI[i]) ioOutputCPI(lpIO,oaCPI[i]/nCPI[i]);
    k=0;
    for(c=0;c<lpCFG->nCamera;c++)                     // check/update measurement In/Out specs
        for(i=0;i<nITEMS;i++)                         // loop over all cameras and measurement attributes
            if(lpAlm->msg[s][c][i])  { k=1; c=nCAMERA; break; }
    if(k!=lpAlm->curSpecWarn[s])  {                   // if warning (alarm light) status changed
        ...                                           // update status
        }
    }
    //--- end of loop-over stretch
    if(maCalc[0]||maCalc[1])  {                       // moving avg calculated for at least 1 stretch line
        ...                                           // update trend window
        }
    ...
EXIT:
    if(err || InTimer==2)  {                          // Error stop or User stop
        StartStop(hwnd,0,!err);                       // stop auto measurement first
        if(err)  {                                    // if error stop
            ...                                       // error handling routines
            }
        }
    ...
    }

/*--------------------------------------------------------------------------*/
GetLiveImage int PFAR GetLiveImage(
int    dpi,          // image resolution, determined by camera optics and geometry
HANDLE *h)           // pt to array of handle to image data
{
    HANDLE hMem;
```

FIG. 12C

```
    int     err=IDE_NoMemory;
    if(lpCFG->DigitalOutput)  *h=GetDigitalImage();         // get image data from camera digital output
    else if(hMem=TP_DataOnBoardGet(                         // get image data from frame grabber
                0,0,pBd->data.width-1,pBd->data.height-1)) {
        TGA2DIBmemBoard(hMem,dpi);                          // convert TGA to DIB format
        if(lpCFG->field) {                                  // if field decompose required
            if(FieldDecompose(hMem,h)) err=0;               // no error
        } else { *h=hMem; err=0; }                          // if no decompose, output 1 handle
    }
    return(err);
}
/*-----------------------------------------------------------
Return: TRUE if OK, FALSE if run-out memory error
------------------------------------------------------------*/
int PFAR FieldDecompose(HANDLE src,HANDLE *h)
{
    LPBITMAPINFOHEADER srclpbi=(LPBITMAPINFOHEADER)GlobalLock(src);
    LPBITMAPINFOHEADER dstlpbi[2];
    DWORD memSize,  srcWidthByte=GetwidthByte(srclpbi);
    WORD  headSize=(WORD)srclpbi->biSize+(WORD)srclpbi->biClrUsed*sizeof(RGBQUAD);
    WORD  dy[2];
    BYTE  _huge* s, _huge* d[2];
    int   _i, k, rtn=TRUE;

dy[0]=((WORD)srclpbi->biHeight+1)>>1;                   // destination image1 height
    dy[1]= (WORD)srclpbi->biHeight-dy[0];                   // destination image2 height
    h[0]=h[1]=NULL;
    for(i=0; i<2; i++) {                                    // allocate memory buffers and copy image header data
        memSize=(DWORD)headSize+(DWORD)dy[i]*srcWidthByte;
        if(h[i]=GlobalAlloc(GMEM_MOVEABLE,memSize)) {
            dstlpbi[i]=(LPBITMAPINFOHEADER)GlobalLock(h[i]);
            _fmemcpy(dstlpbi[i],srclpbi,headSize);          // copy image head info
            dstlpbi[i]->biHeight=dy[i];
            dstlpbi[i]->biSizeImage=dstlpbi[i]->biHeight*srcWidthByte;
            d[i]=PointToData(dstlpbi[i]);
        } else rtn=FALSE;
    }
    if(rtn) {
        s=PointToData(srclpbi);                             // point to source image data
        k=(int)srclpbi->biHeights2;                         // even/odd field index
        for(i=0; i<(int)srclpbi->biHeight; i++) {           // change field index alternatively
            k=!k;
```

FIG. 12D

```
        _fmemcpy(d[k],s,(WORD)srcWidthByte);// copy image data from source to destination
        d[k]+=srcWidthByte;                 //  advance point to next image data row of destination image
        s   +=srcWidthByte;                 //  advance point to next image data row of source image
        }
    GlobalUnlock(h[0]);
    GlobalUnlock(h[1]);
    } else if(h[0]) { GlobalUnlock(h[0]); GlobalFree(h[0]); h[0]=NULL; }
    GlobalUnlock(src);
    return(rtn);
}
/*------------------------------------------------------------------------------------------*/
Return: 0 if OK, IDE_?? if Fail
------------------------------------------------------------------------------------------*/
static int PNEAR MeasureCrimpAuto(
HWND hwnd,              // handle to caller's window
int sId,int cId)        // stretch and camera ID
{
    if(pref.UndoEnable&&(PtActWnd->DIB2=DIBDupFull(PtActWnd->DIB))==NULL) return(IDE_NoMemory);
    lpRes->avgIntensity=TowEdgeDetection(PtActWnd->DIB,1);
    if(lpCFG->prep[1].smooth) {          // pre-process image if noise reduction is enabled
        LPBITMAPINFOHEADER lpbi=(LPBITMAPINFOHEADER)GlobalLock(PtActWnd->DIB);
        Filter(hwndStatus,0,lpbi,PtActWnd->DIB2,0,lpCFG->prep[1].x,lpCFG->prep[1].y,SMOOTH_AVERAGE,0,0,0,0f);
        GlobalUnlock(PtActWnd->DIB);
        }
    FindCrimp(PtActWnd->DIB,lpCFG->prep[1].bandsize,lpCFG->prep[1].showBand);  // identify/validate crimps
    if(lpCtl->nLogdata==1) return(WriteLog(sId,cId));   // log measurement result to a disk file
    return(0);
}
/*------------------------------------------------------------------------------------------*/
Return: 0 if OK, IDE_?? if Fail
------------------------------------------------------------------------------------------*/
static void PNEAR FindCrimp(
HANDLE memSrc,          // src image to find crimp
int    bandsize,        // user-specified band size
char   showBand)        // user-specified show band-avged image option
{
    LPBITMAPINFOHEADER lpbi=(LPBITMAPINFOHEADER)GlobalLock(memSrc);
    LPINT  Loc=lpRes->Loc;      // pointer to pre-allocated memory buffer for storing location Info
    LPBYTE Pxl=lpRes->Pxl;      // pointer to pre-allocated memory buffer for storing pixel intensity of the profile
    DWORD  ByteWidth=GetWidthByte(lpbi);   // # of byte per image data row
    DWORD  bandByte =ByteWidth*bandsize;   // # of byte per band of image data
    int    Width=(int)lpbi->biWidth;       // image width in pixel
```

FIG. 12E

```
BYTE    _huge* srcD, _huge* d;                                          // point to src image data
int     nBand, b;                                                        // # of band to process
int     i, k, first, N, ext, cpi;                                        // loop control variables
LONG    mArea,mCunt,nArea,nCunt,lArea,lCunt;                             // area and counter for micro/normal/large crimp
LONG    tArea,tCunt;                                                     // total area and counter
register WORD pv;                                                        // pixel value for(i=0;i<cpiHighLimit;i++) lpRes->pHist[i]=0;                           // init. distribution data buffer
mArea=nArea=lArea=mCunt=nCunt=lCunt=0L;                                  // init. area and counter variables
if(!lpRes->avgIntensity) {
    N=lpRes->top-lpRes->bottom;                                          // # image rows, excluding background
    nBand=N/bandsize;                                                    // # of band to process
    srcD=PointToData(lpbi)+ByteWidth*lpRes->bottom;                      // point to src image data
} else { N=nBand=0; }                                                    // black image, or all background
lpRes->edge=100.0f*(1.0f-(float)N/(float)lpbi->biHeight);
b=nBand;                                                                 // # of bands to process
while(b--) {                                                             // loop over bands
    d=srcD+i; pv=(WORD)*d;                                               // calculate banded avg
    for(k=1;k<bandsize;k++) { d+=ByteWidth; pv+=(WORD)*d; }
    Loc[i]=(int)(pv/bandsize);
    Pxl[i]=(BYTE)Loc[i];
    if(showBand) {
        d=srcD+i; pv=(BYTE)*d=(BYTE)pv;
        for(k=1;k<bandsize;k++) { d+=ByteWidth; *d=(BYTE)pv; }
    }
}
if((N=FindPeakValley(Loc,Width,&first))>2) {                             // at least 2 points
    N=IdentifyPeak(Loc,Pxl,N,first,cPkInt)-1;                            // -1 for not checking the last one
    for(i=0;i<N;i++) {
        ext=Loc[i+1]-Loc[i];                                             // distance between adjacent peaks.
        cpi=(int)(dpiAdj)/(float)ext);                                   // convert to cpi unit
        if(cpi>=cpiLowLimit && cpi<cpiHighLimit) lpRes->pHist[cpi]+=1;
        if(     ext<=cNone) continue;                                    // not counted if too small
        else if(ext<=cMicr) { mArea+=ext; mCunt++; }                     // micro crimp
        else if(ext<=cNorm) { nArea+=ext; nCunt++; }                     // normal crimp
        else if(ext<=cLarg) { lArea+=ext; lCunt++; }                     // large crimp
        else continue;                                                   // not counted if too large
        d=srcD+Loc[i];                                                   // init. image data pt to draw mark
        for(k=0; k<ext; k++) *d++=0xff;                                  // low horizontal line
        d=srcD+Loc[i];
        for(k=0; k<bandsize; k++) {                                      // mark found crimp
```

FIG. 12F

```
            *d=0xff; *(d+ext)=0xff; d+=ByteWidth;
        }
        srcD+=bandByte;
    }
    if(mArea) lpRes->m[0]=dpiAdj*(float)mCunt/mArea; else lpRes->m[0]=0.0f;     // micro crimp cpi
    if(nArea) lpRes->n[0]=dpiAdj*(float)nCunt/nArea; else lpRes->n[0]=0.0f;     // normal crimp cpi
    if(lArea) lpRes->l[0]=dpiAdj*(float)lCunt/lArea; else lpRes->l[0]=0.0f;     // large crimp cpi
    if(tArea=mArea+nArea+lArea) {
        tCunt=mCunt+nCunt+lCunt;                                                 // total crimped area
        lpRes->o[0]=dpiAdj*(float)tCunt/(float)tArea;                           // total crimp count
    } else lpRes->o[0]=0.0f;                                                    // overall CPI
    if(tArea=(LONG)nBand*Width) {                                               // total image area excluding background area
        lpRes->m[1]=100.0f*(float)mArea/tArea;                                  // %Area covered: micro
        lpRes->n[1]=100.0f*(float)nArea/tArea;                                  // %Area covered: normal
        lpRes->l[1]=100.0f*(float)lArea/tArea;                                  // %Area covered: large
    } else { lpRes->m[1]=lpRes->n[1]=lpRes->l[1]=0.0f; }
    lpRes->o[1]=lpRes->m[1]+lpRes->n[1]+lpRes->l[1];                            // %Area covered: Overall
    ShowResult(hwndCrimp);                                                       // display result
}

/*---------------------------------------------------------------------------
Returns: # of peak/valley points found in the array
-----------------------------------------------------------------------------*/
int PFAR FindPeakValley(
int loc[],        // input array, replaced with location idx of peak/valley points found upon return
int nIn,          // # of point in the array
int *VPlst)       // +/- = the 1st peak-valley point is peak/valley
{
    register int old, new;
    int nEqu;                  // # of equal value points
    int nOut=0;                // # of peak/valley point in the array
    int i, sign;
    old=loc[0]; nEqu=0;
    for(i=1; i<nIn; i++) {
        if(loc[i]!=old) {
            sign=(loc[i]>old)?1:-1;                                              // initial slope sign
            *VPlst=-sign;
            loc[nOut++]=nEqu>>1;                                                 // location index of 1st peak/valley point
            break;                                                               // break-out search for 1st point
        } else nEqu++;
```

FIG. 12G

```
        old=loc[i]; nEqu=0;
        if(i<nIn) {
            for(i=i+1; i<nIn; i++) {
                new=loc[i];
                if(new!=old) {
                    if((new>old && sign<0) ||
                       (new<old && sign>0)) {
                        loc[nOut++]=i-1-(nEqu>>1);        // valley point
                        sign=-sign;                        // peak point
                                                           // record this turning point
                    }
                    nEqu=0;
                } else nEqu++;
                old=new;
            }
            loc[nOut++]=(nIn-1)-(nEqu>>1);                // the last peak/valley point
        }
        return(nOut);
    }

/*----------------------------------------------------------------------
Identify crimp based on intensity criteria 'threshold'
Idx to crimp peak is returned via input peak/valley idx array 'loc[]'
------------------------------------------------------------------------*/
int PFAR IdentifyPeak(
int   loc[],       // input peak/valley index array, return Peak idx array
BYTE  pxl[],       // pixel intensity value array
int   N,           // # of peak/valley in array 'loc'
int   first,       // >0, 1st index in array 'loc' points to a peak
int   threshold)   // intensity threshold value
{
    int i, outN=0;
    int C, L, R;             // current peak idx, left- & right-side valley idx
    int cPxl;                // current peak pixel intensity
    int NoCompare=1;         // when previous peak is identified as NOT crimp peak
                             // higher one of the previous and current peaks should
                             // be used for identifying crimp peak i=(first>0) ? 2 : 1;     // 1st peak to be examined, 1st idx point to a peak if first>0
    L=loc[i-1];              // idx to left-side valley
    if((N-i)%2) N--;         // the last location is peak which should NOT be checked
                             // because no right-side valley to be compared for(; i<N; i+=2) {
        if(NoCompare || pxl[C]<pxl[loc[i]]) C=loc[i];
```

FIG. 12H

```
cPxl=(int)pxl[C]-threshold;
R=loc[i+1];
NoCompare=1;              // default to use new peak value @ next time peak identification
if(cPxl>=(int)pxl[L]&&cPxl>=(int)pxl[R]) {    // crimp peak found
    loc[outN++]=C;                // record idx in output array
    L=R;                          // right-side valley becomes left-side valley for next peak
} else {                          // crimp peak Not found
    if(pxl[R]<pxl[L]) L=R;        // right-side valley is lower, use it as left-side valley @ next time
    else NoCompare=0;             // left-side valley is lower, need compare for highest peak @ next time
}
}
return(outN);
}
```

APPARATUS AND METHOD FOR CHARACTERIZING FIBER CRIMPS

This application is a continuation of allowed application Ser. No. 09/621,845, filed Jul. 24, 2000 which is now U.S. Pat. No. 6,674,887 issued on Jan. 6, 2004.

BACKGROUND OF THE INVENTION

1. Field of the Invention

This invention relates generally to an apparatus and a method for measuring crimp characteristics of fibers; more specifically, an apparatus and method for characterizing fibers in a moving crimped tow.

2. Description of the Prior Art

Manufactured or synthetic fiber filaments are usually crimped into a tow before being cut into staple for further processing for various uses such as tops, slivers or yarns. The fibers are usually crimped by passing the fibers through a crimping apparatus to produce waves or crimps. The quality of manufactured fibers is often measured by crimp characteristics such as crimp uniformity, number of crimps per inch, crimp frequency, etc. Until recently, the crimp properties have been measured by manual examination of a cut portion of fiber, for example, by counting the number of crimps per unit length.

It follows that automated systems for measuring crimp characteristics would greatly improve the speed and accuracy in characterizing the fibers, enabling on line adjustments in the production process, and the production of fiber staple according to specifications.

Various types of automated systems for measuring crimp characteristics have previously been proposed. Generally, the systems include a light source for illuminating the crimped tow; a photographic element for acquiring an image of a portion of the crimped tow; circuitry for processing the acquired image; and a display for displaying the measured crimp characteristics.

One type of system employs a conventional TV camera to acquire the image of the moving crimped tow. As is apparent to one skilled in the art, a TV camera captures an image pattern and converts the image as electrical charges corresponding to the brightness levels of the moving crimped tow. The charges are converted to a video signal in a sequential order of picture elements. The picture elements are displayed on a monitor as an interlaced raster scan, e.g., the picture elements are swept horizontally from top to bottom. In interlaced scanning, two fields are used.

After completion of the first field scan from top to bottom, the beam is blanked as it returns to the top where the process is repeated to provide a second field scan. Due to the half-line offset for the start of the beam return to the top of the raster and for the start of the second field, the lines of the second field line lie in between the lines of the first field. Thus, the lines of the two are interlaced. The two interlaced fields constitute a single video frame.

A problem exists with using a conventional TV camera to acquire images of a moving crimped tow. The acquired image is not a true representation of the actual image, because the tow is moving. The two fields which are interlaced are obtained from two different areas of the tow. By the time the beam returns to the top of the raster to start scanning the second field, the tow has moved and a different portion of the tow is scanned. Therefore, measured results derived from the interlaced images depart from the true images.

A common approach used to counteract the above problem associated with the use of a conventional TV camera is by use of a synchronized strobing system. A stroboscopic light source emits a light pulse which creates an apparent stopped motion view of the moving crimped tow. The camera is synchronized to take a snap shot of the moving crimped tow when the light pulse is emitted. A synchronized strobing system effectively freezes the moving crimped tow and the two interlaced fields do not produce an erroneous image as in using a non-strobed system. However, advanced electronics are required for the synchronization controls. Further, in order to cover an entire width of the moving tow when using a synchronized strobing system, movement of the focused strobe light source and/or the camera may be necessary, and positioning mechanisms such as stepping motors and controls are involved. If light or camera movement is required, extra time is needed to position the devices, making on-line or real-time measurements and/or device adjustments difficult if not impossible. Examples of strobed-based apparatus for measuring crimp characteristics of fibers in a moving crimped tow are disclosed in U.S. Pat. Nos. 4,737,846; 4,415,926; 4,232,336; 4,240,110; and 5,351,308.

A need therefore exists for an apparatus which uses a continuous or non-strobed system for acquiring images of a moving crimped tow which is devoid of the above problems and is also capable of on-line or real-time measurements and/or system adjustments and does not require decomposition means.

SUMMARY OF THE INVENTION

The present invention relates to an improved apparatus and method for measuring crimp characteristics of fibers in a moving crimped tow where a progressive scanning camera is used to acquire a non-interlaced video image of the moving crimped tow. A continuous light source illuminates the crimped tow while the camera acquires the non-interlaced image. A computer processor and its associated software processes the acquired non-interlaced image.

The processor and the stored software converts the acquired non-interlaced image into a series of horizontal bands. The bands are analyzed to measure the crimp characteristics of the section of moving crimped tow represented by the bands. The measured results may be displayed and adjustments may be made to peripheral devices which in turn control the manufacturing process to correct deviations from the operator-specified specifications. The processor and stored programs processes the image into user defined categories and the frequency of the crimps belonging in each category is displayed on a monitor for allowing the operator to determine whether the crimped tow is within the predetermined specifications.

A method of the invention includes the steps of acquiring a non-interlaced video image of a crimped tow; digitizing the acquired non-interlaced image; and processing the image. In one embodiment, digitization of the image is accomplished by the progressive scanning camera itself. In another embodiment, digitization is accomplished by the use of a frame grabber.

An illustrative approach according to the present invention in the step of processing the non-interlaced image includes: dividing the image into a series of horizontal bands; constructing an intensity profile by averaging the pixel intensity of each band; identifying local minima and maxima of the intensity profile, and labeling a maximum as a crimp peak if the difference in intensity between the maximum and its two immediate neighboring minima exceeds an operator-specified intensity threshold value; calculating and storing the distance of neighboring crimp peaks for all peaks identified in the above step; and grouping the crimp peaks into a crimp type category.

A preferred method further includes the step of communicating measurement results to a plurality of peripheral devices which configure the manufacturing process of the crimped tow.

Advantageously, the apparatus and method of the present invention also provide convenient and reliable means for monitoring the quality of a crimped tow to obtain physical data therefrom which can be used as a quality control measure during the manufacturing process. For a traditional batch-type manufacturing process, the system also supports a start-up mode process for minimizing production waste.

BRIEF DESCRIPTION OF THE DRAWINGS

Preferred embodiments of the invention are described hereinbelow with reference to the drawings Wherein:

FIGS. 6a and 6b are representative illustrative monitor displays of representative crimp criteria and system settings for a preferred crimp measurement apparatus for a manual and an automatic operating mode, respectively, according to the present invention.

FIGS. 7a, 7b, 7c, 7d and 7e are representative illustrative setting displays for the automatic operating mode.

FIGS. 11a, 11b, 11c, and 11d are screen depictions showing representative illustrative analog and digital I/O test diagnostics for the illustrative crimp measurement system according to the present invention.

FIGS. 12a, 12b, 12c, 12d, 12e, 12f, 12g and 12h list a representative portion of the stored program including program for implementing the method as outlined in FIG. 2.

DETAILED DESCRIPTION OF PREFERRED EMBODIMENTS OF THE INVENTION

An illustrative crimp measurement system of the present invention is a digital image analysis based system for characterizing fiber crimps including quantifying the number of crimps per unit length and crimp size distribution of a moving crimped tow. The measurement, which is non-contact and non-destructive, can be conducted off-line or on-line during the yarn manufacturing process at which a crimped tow moves at high speeds, for example, around 1,200 feet per minute.

Figure 1A:
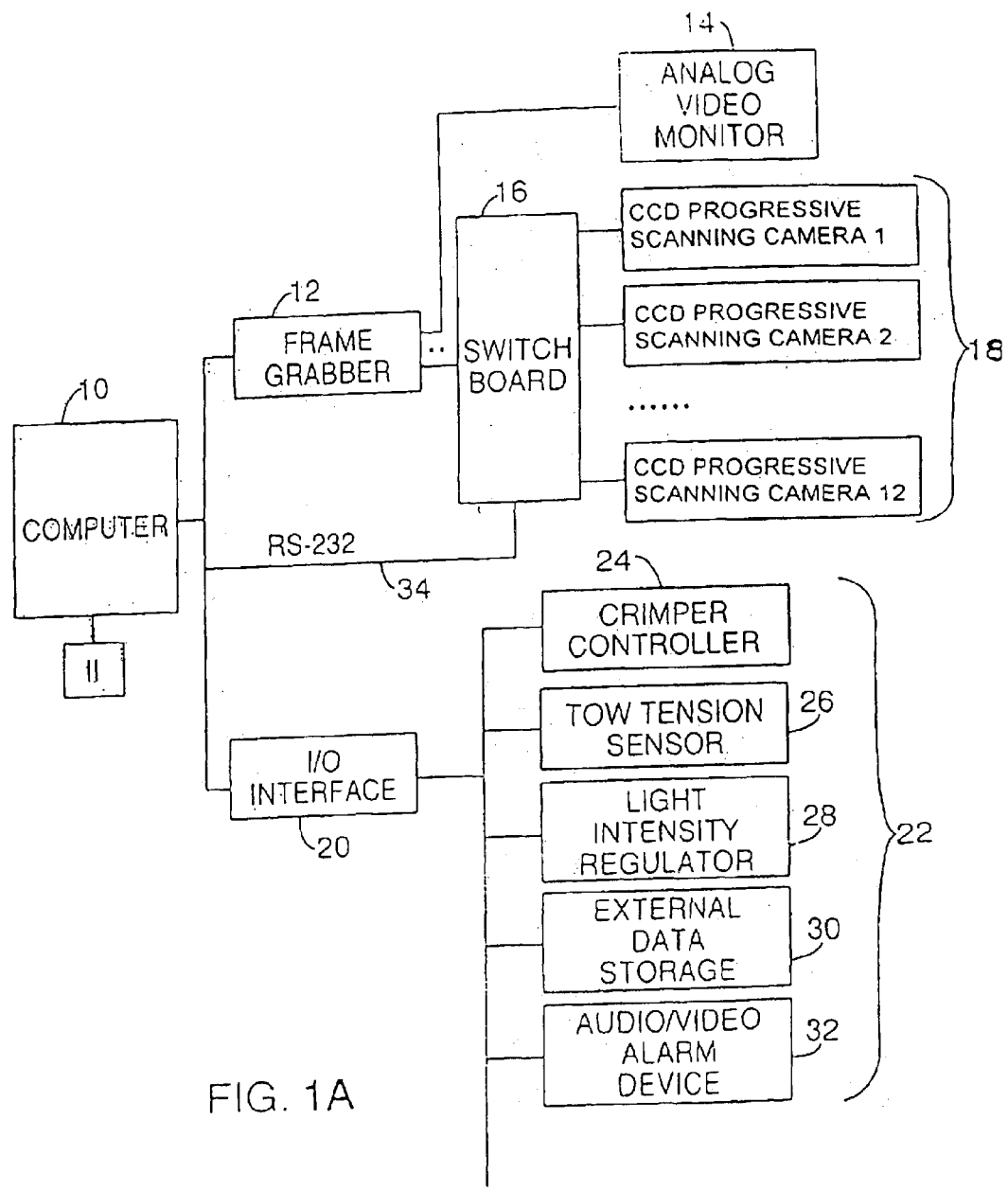
FIGS. 1a and 1b are block diagrams of the major components for measuring fiber crimp characteristics according to two preferred embodiments of the present invention.

Referring to FIG. 1a, one embodiment of the illustrative crimp measurement system according to the present invention includes a computer 10, a frame grabber 12, an analog video monitor 14, a switch board 16 that accepts analog signals, a plurality of progressive scanning video cameras 18, an I/O interface 20, and peripheral devices 22.

Figure 1B:
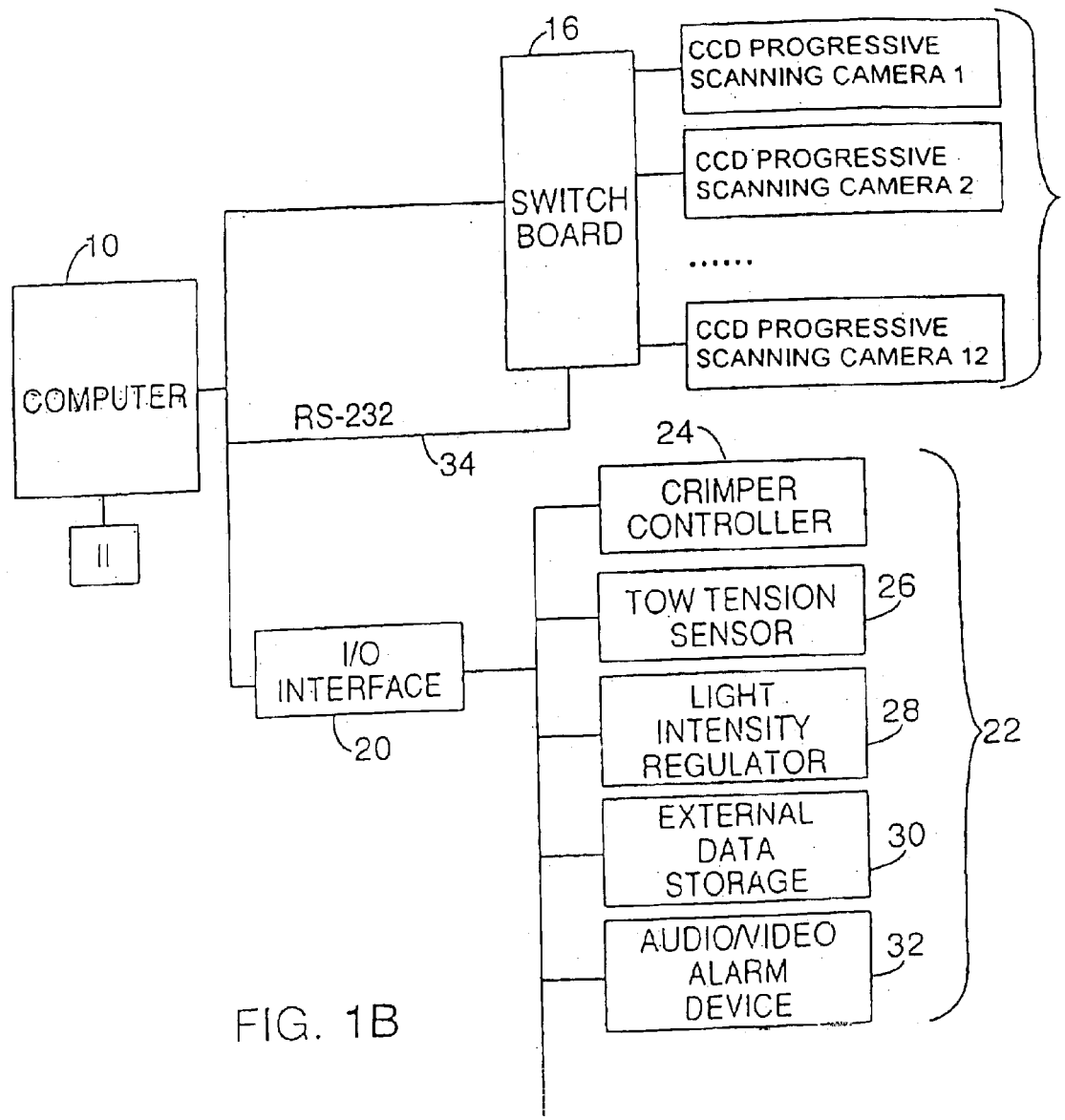

Referring to FIG. 1b, a second embodiment of the illustrative crimp measurement system according the present invention includes a computer 10, a switch board 16 that accepts digital signals, a plurality of progressive scanning video cameras 18, an I/O interface 20, and peripheral devices 22. In this embodiment, during initial set up of the system, including focusing of the cameras, an analog video monitor may optionally be directly connected to the plurality of progressive scanning video cameras and their output temporarily switched to analog signal. However, one can use the computer screen during set up although there may be a delay between adjusting camera focus and the resultant change in the image on the computer screen.

In both embodiments, the peripheral devices 22 include, but are not limited to, a crimper controller 24, a tow tension sensor 26, a light intensity regulator 28, an external data storage 30, and an audio/video alarm device 32.

The switch board 16 may be interfaced to the computer 10 by a RS-232 cable 34, and the plurality of progressive scanning video cameras 18 for directing a signal to the computer 10 from the plurality of progressive scanning video cameras 18 mounted at different positions across a tow or at different tow stretch lines. The I/O interface 20 is connected to the peripheral devices 22 for I/O communication between the computer 10 and peripheral devices 22.

The computer 10 is preferably an IBM compatible PC which includes a Pentium-type microprocessor and operates in Microsoft Windows environment. The computer 10 includes software in the form of stored program 11 for controlling the hardware components of the system. The switch board 16 is preferably a model capable of accommodating up to 12 video cameras. Through computer 10, an operator sends signals via RS-232 cable 34 to the switch board 16 to selectively receive signal from one of cameras 18. The selection process may be by a multiplexing scheme commonly used by one skilled in the art. The I/O interface 20 constitutes at least one data acquisition board having sufficient analog and digital channels for I/O communications between the computer 10 and the peripheral devices 22. The frame grabber is preferably capable of digitizing an analog video image into a two-dimensional array of data.

The video cameras 18 are preferably Pulnix TM-9700 series cameras with progressive scanning capacity and electronic shutter speed control. The image acquired directly by camera 18 may be a progressive scan image which is therefore non-interlaced. Thus, advantageously, the need for decomposition of an acquired interlaced image into odd and even fields is obviated. Although the camera can output an interlaced image, this capacity is not used in the instant invention. Pulnix TM-9700 series cameras may output either an RS-170 analog signal or an RS-422 digital signal. In an embodiment in which the camera outputs a video signal, switch board 16 accepts video signal and frame grabber 12 digitizes the signal. In an alternate embodiment in which the camera outputs a digital signal, switch board 16 accepts digital signal. The latter embodiment is advantageous in not requiring the frame grabber for digitization functionality thus reducing the number of elements in the overall system. Any other appropriate progressive scanning CCD camera may be utilized in the invention.

User interfaces include a main control panel, a display of measurement results on the computer screen, a keyboard or a mouse, and selection icons on the computer display for allowing an operator to configure the crimp measurement system, as discussed further below.

A light source (not shown) is positioned proximate the plurality of progressive scanning video cameras 18 for continuously illuminating the moving crimped tow. The light source is preferably a halogen flood light lamp having intensity adequate to cover the full width of a tow line. The intensity of the light source may be adjusted by light intensity regulator 28 which in turn is under control by processor 10 and stored program 11. At least one tow stretch line (not shown) is positioned below the light source for moving the crimped tow. The illustrative components of FIG. 1 may characterize three or more tow lines. The tow stretch line may be stationary but preferably moves the crimped tow at speeds up to around 1,200 feet per minute.

Figure 2:
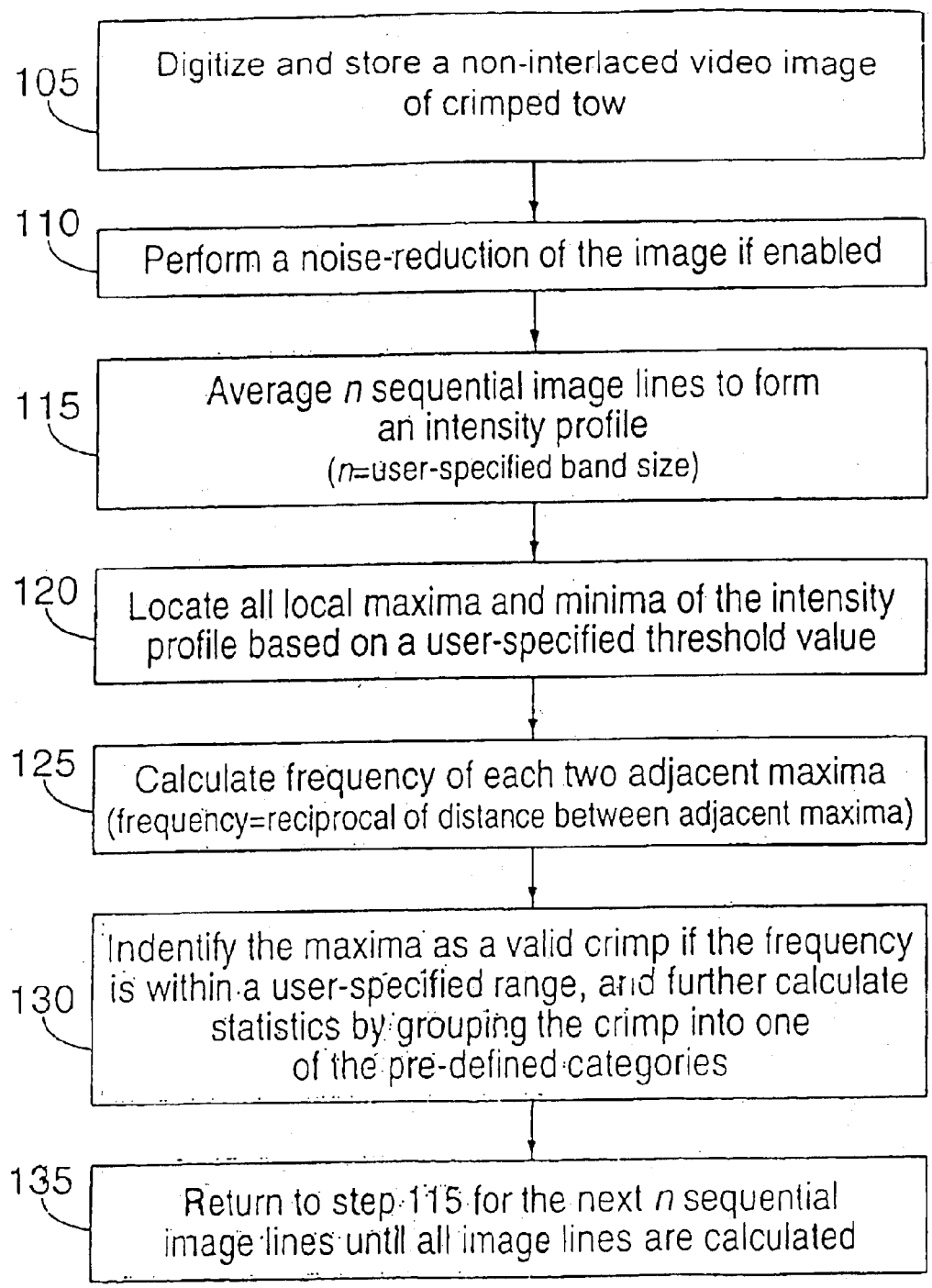
FIG. 2 is a flow chart illustration of a method of measuring the fiber crimp characteristics according to the present invention.

FIG. 2 illustrates an algorithmic process of stored program 11 for measuring the crimp characteristics of the moving crimped tow. Under software control, the moving tow is continuously illuminated by the light source. Progressive scanning video cameras 18 are preferably stationary and may be enabled for continually capturing images of the stationary or moving crimped tow, and signals representing selected images from one of cameras 18 are received by the computer 10 upon selection by switch board 16 under control by stored program 11.

In the embodiment in which the camera outputs digital signal, the selected image may be stored directly in computer 10 in step 105. In the embodiment in which the camera outputs video signal, the selected image is first digitized by the frame grabber 12 and then may be stored in computer 10 in step 105.

A representative portion of stored program 11 including program codes for implementing the process as described in FIG. 2 is shown in FIGS. 12a, 12b, 12c and 12d:

Noise-reduction of the non-interlaced image by conventional image noise-reduction techniques such as the use of a filter is performed in step 110. This process is optional and may be disabled by the operator via the setting displays of FIGS. 6a and 6b.

Each non-interlaced image will typically have 400 lines. For purposes of measuring crimp characteristics, the lines are divided into M bands, each band having N lines. For example, M is set at 50 and N at 8. Thus, each non-interlaced image has 400 lines, 50 bands with 8 lines in each band. If there are a different number of lines in the non-interlaced image, the values of M and N will be adjusted appropriately. The value of N is preferably at least 4.

In step 115 each band is averaged to form an intensity profile, which is represented in a gray level scale ranging from 0 (black) to 255 (white). Step 120 locates all local maxima and minima crimp peaks of the intensity profile based on the operator-specified crimp intensity threshold. A crimp peak is labeled as a maximum if the difference in its intensity and the intensity of its two immediate neighboring crimp peaks exceed an operator-specified intensity threshold value. The crimp intensity threshold value is adjusted with a web material-related optical factor which takes into consideration the absorption and reflection qualities of the web material.

The crimp intensity threshold is entered into the system via a crimp measurement setting display, such as shown in FIG. 6a. The crimp intensity threshold in FIG. 6a has been set to eight.

The frequency of adjacent maxima crimp peaks is calculated in step 125, where frequency is defined as the reciprocal of the distance between two adjacent maxima. In step 130 each maxima is identified as a valid crimp if its corresponding frequency is within a user-specified range.

Each crimp is grouped into one of the three pre-defined categories, which include micro, normal and large. The grouping is determined based on an operator-specified CPI range for each of the three categories via one of the system measurement setting displays depicted by FIGS. 6a and 6b. As an example, in FIGS. 6a and 6b a crimp is categorized as micro, normal or large if the CPI parameter is greater or equal to 16, 8, or 4, respectively.

Statistical analysis is performed on the measured results to determine parameters such as average CPI and the percent of area covered by crimps categorized in each category. The statistical analysis is displayed on the computer screen to enable the operator to view the data as further discussed below.

Steps 115 to 130 are repeated for each band until all image lines of the noninterlaced image have been analyzed (135).

To capture images representing the entire width of the crimped tow, which is usually about four inches or more, more than one camera may be used. In the present illustrative embodiment, three cameras are used for each tow line. The same steps 105 to 135 of FIG. 2 are followed in analyzing the images acquired by the other cameras to obtain the crimp statistics for the entire width of the moving crimped tow. The data from all the three progressive scanning cameras 18 is averaged to get the overall crimp measurement results. These results along with other statistical analysis results are displayed on the computer screen for allowing the operator to examine the crimp characteristics of the crimped tow.

Figure 8:
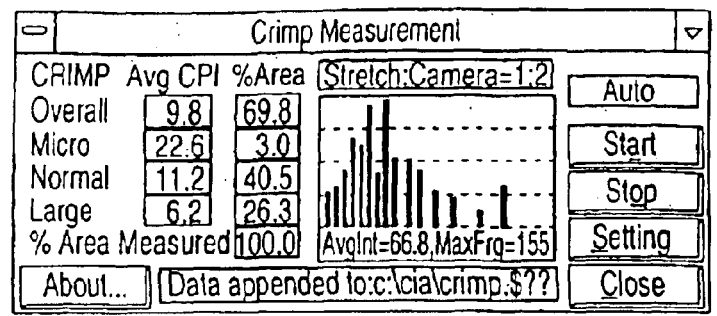
FIGS. 8 and 9 are screen depictions showing representative illustrative crimp measurement results in text and in graphs.
Figure 9:
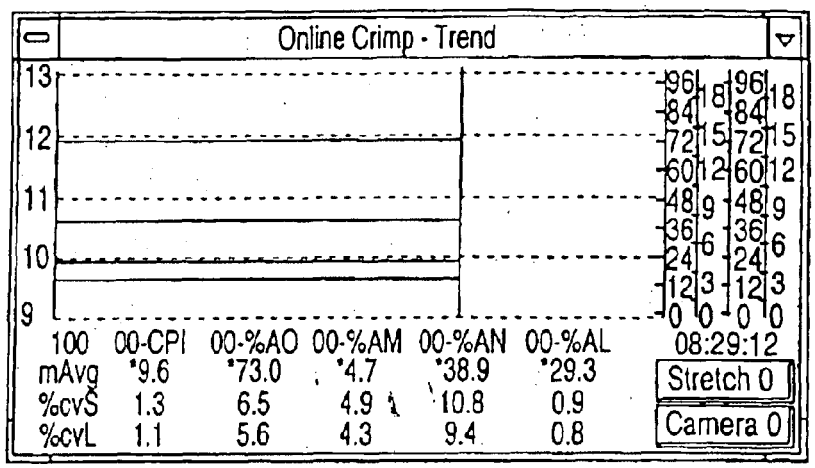
Figure 10:
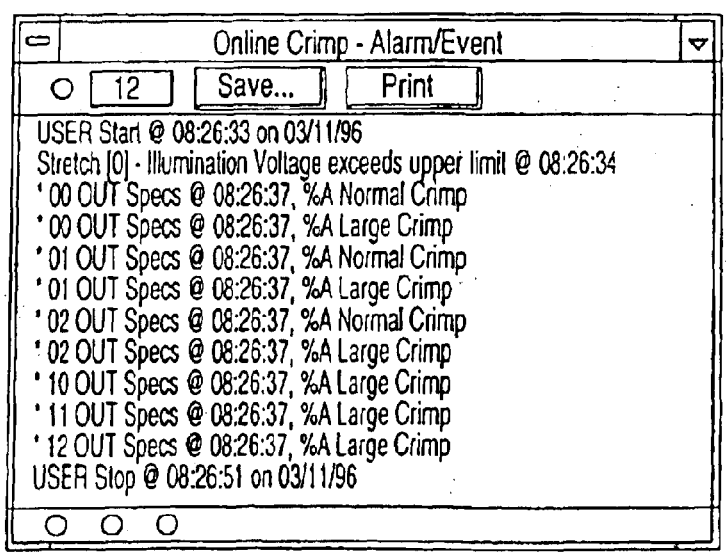
FIG. 10 shows a representative display of illustrative alarm events.
Figure 11A:
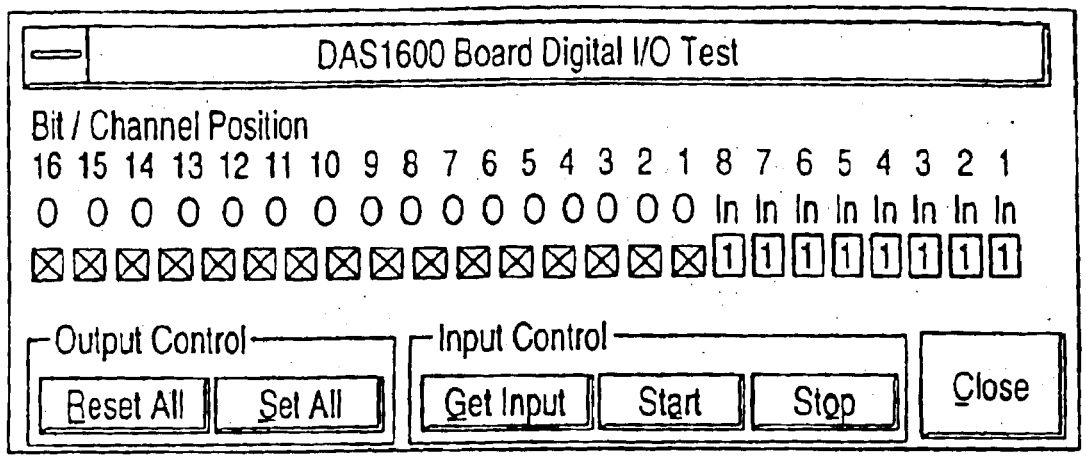
Figure 11B:
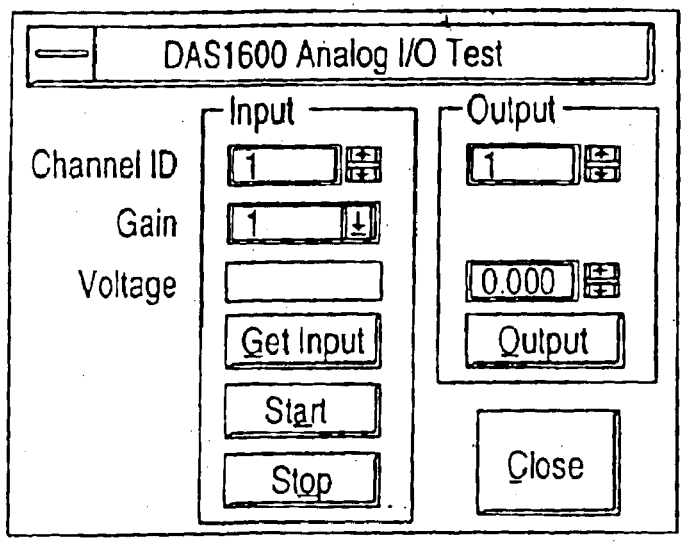

FIGS. 8 and 9 are exemplary screen depictions of crimp measurement results. FIG. 8 indicates that the average CPI is 9.8 for the overall tow, and 22.6, 11.2, and 6.2 for the crimps categorized in the micro, normal and large categories, respectively. FIG. 8 further indicates that the percentage of tow area covered by measurable crimp is 69.8%, and that 3.0%, 40.5%, and 26.3% of the area is covered by crimp categorized in the micro, normal and large categories, respectively. The screen depiction of FIG. 8 further includes a main user interface control panel on the right side for controlling the crimp measurement system and setting system parameters.

FIG. 9 indicates the online crimp distribution statistics for a crimped tow. These distribution statistics change as the crimp measurement process proceeds to enable the operator to continuously monitor the crimp measurements of the moving crimped tow. The online crimp distribution screen also indicates the moving crimp average (mAvg), the percent of area covered by crimp in each of the three categories and the overall area covered by crimp, along with other data.

The operator in viewing the measured results can direct peripheral devices 22 via I/O interface 20 to take appropriate actions to conform the manufacturing process of the crimped tow to the proper product and process specifications. As an example, the operator can instruct crimper controller 24 to increase or decrease the amount of crimps or to reconfigure the manufacturing process to reallocate the number of crimps categorized as micro, normal and large, depending on the contemplated use of the crimped tow.

With reference to system measurement setting displays depicted by FIGS. 6a and 6b, the operator can select either manual or automatic as the operating mode, as shown on the top left-hand side of FIGS. 6a and 6b. In FIG. 6a the manual operating mode is selected and in FIG. 6b the automatic operating mode has been selected. Other initial settings or adjustments for the crimp measurement system can be made with the aid of setting displays depicted by FIGS. 6a–6b. For example, parameter adjustments or settings can be made for image resolution, band size, crimp intensity threshold, valid crimp per inch (CPI) range, overall CPI set point, CPI tolerance; tow stretch line select and camera select crimp types and specifications; and image pre-process configuration.

On the bottom left-hand side of FIGS. 6a and 6b, the operator can select whether to apply smoothing to the acquired image before it is processed. If smoothing is selected then each non-interlaced image is passed through a filter to perform a noise-reduction of the image as discussed above. The amount of image lines which constitute a band is also selected in the same box labeled "Image Pre-process." In FIG. 6a the selected band size is eight and in FIG. 6b the selected band size is four.

In the system measurement setting display depicted by FIG. 6b in which the automatic mode has been selected, the number of tow stretch lines which have been selected for measurement is three. The number of cameras which have been selected for each tow stretch line is also three. Directly below the selections for the number of tow stretch lines and cameras for each tow stretch line is a user interface for accessing the system setting displays depicted by FIGS. 7a–7e for the automatic operating mode.

Figure 7A:
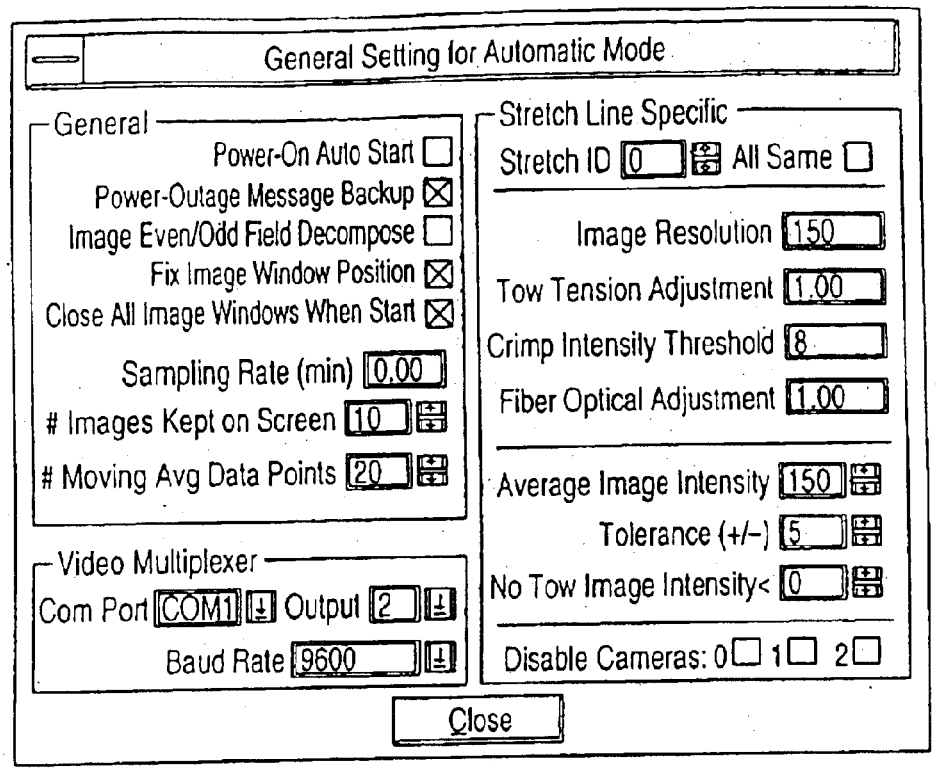

By selecting the square marked "General" the General Setting for Automatic Mode setting display depicted by FIG. 7a is accessed. This setting display allows the operator to set the general system setting and various parameters, such as: the sampling rate, the number of images which are kept on the screen, the number of moving average data points, the image resolution, the tow tension adjustment factor, the crimp intensity threshold, the fiber optical adjustment factor, the average image intensity, the tolerance factor, and the no tow image intensity. As shown in FIG. 7a, the operator will not select image even/odd field decompose for use with the progressive scanning camera of the invention.

Figure 7B:
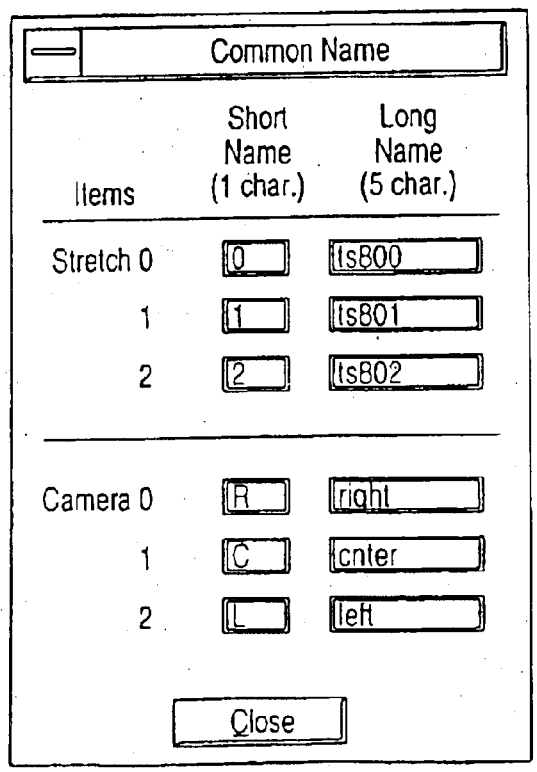

By selecting the square marked "Alias" in FIG. 6b, the Common Name setting display depicted by FIG. 7b is accessed. This setting display allows the operator to provide a short and long name for each tow stretch line and for each camera positioned across the width of the tow stretch lines. As shown by FIG. 7b, the short and long common names for the tow stretch lines are 0, 1, and 2 and ts800, ts801, and ts802, respectively. The short and long common names for the three cameras are R, C, and L and right, center, and left, respectively.

By selecting the square marked "Trend" in FIG. 6b, the Trend Window Setting display depicted by FIG. 7c is accessed. This setting display allows the operator to select the parameters he desires to be displayed during normal measurement. The selected parameters are displayed on an on-line crimp trend window, such as the one depicted by FIG. 9. Using the Trend Window Setting display, the operator can set the ranges for the overall CPI parameter, percent of area covered by overall CPI, and percent of area covered by crimp in the micro, normal, and large categories.

By selecting the square marked "I/O" in FIG. 6b, the I/O Usage Setting display depicted by FIG. 7d is accessed. The display of FIG. 7d allows the operator to manually enable and disable each tow stretch line, the start-up process, the bad-tow alarm, the specifications alarm, the illumination, the tow tension, and set the range for the overall CPI and other parameters. On the right-hand side of FIG. 7d, the operator can enable the system malfunction alarm and run either a digital or analog diagnostic test for each data acquisition board.

Figure 7E:
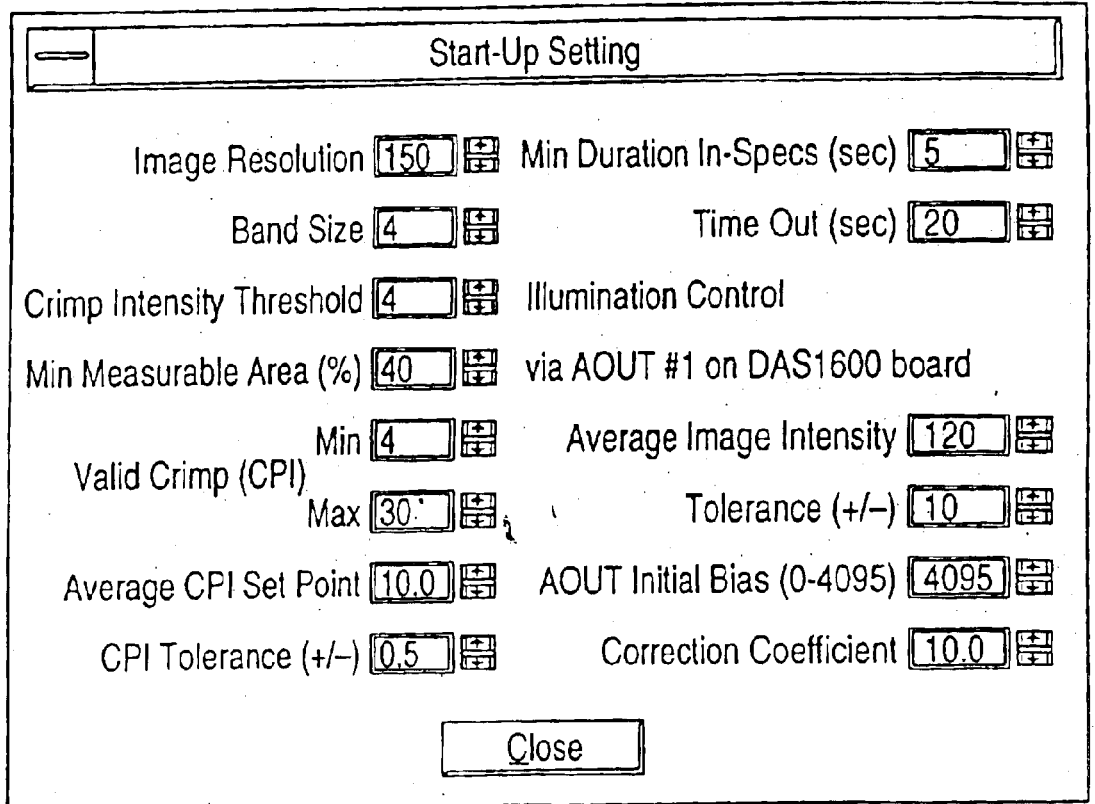

By selecting the square marked "Start Up" in FIG. 6b, the Start-Up Setting display depicted by FIG. 7e is accessed. This display allows the operator to configure a start-up mode process, another advantageous feature of the apparatus which is described below. Through FIG. 7e the operator can set the image resolution, band size, the crimp intensity threshold value, the minimum measurable area, the range for valid crimp, and other start-up mode process parameters.

Figure 3:
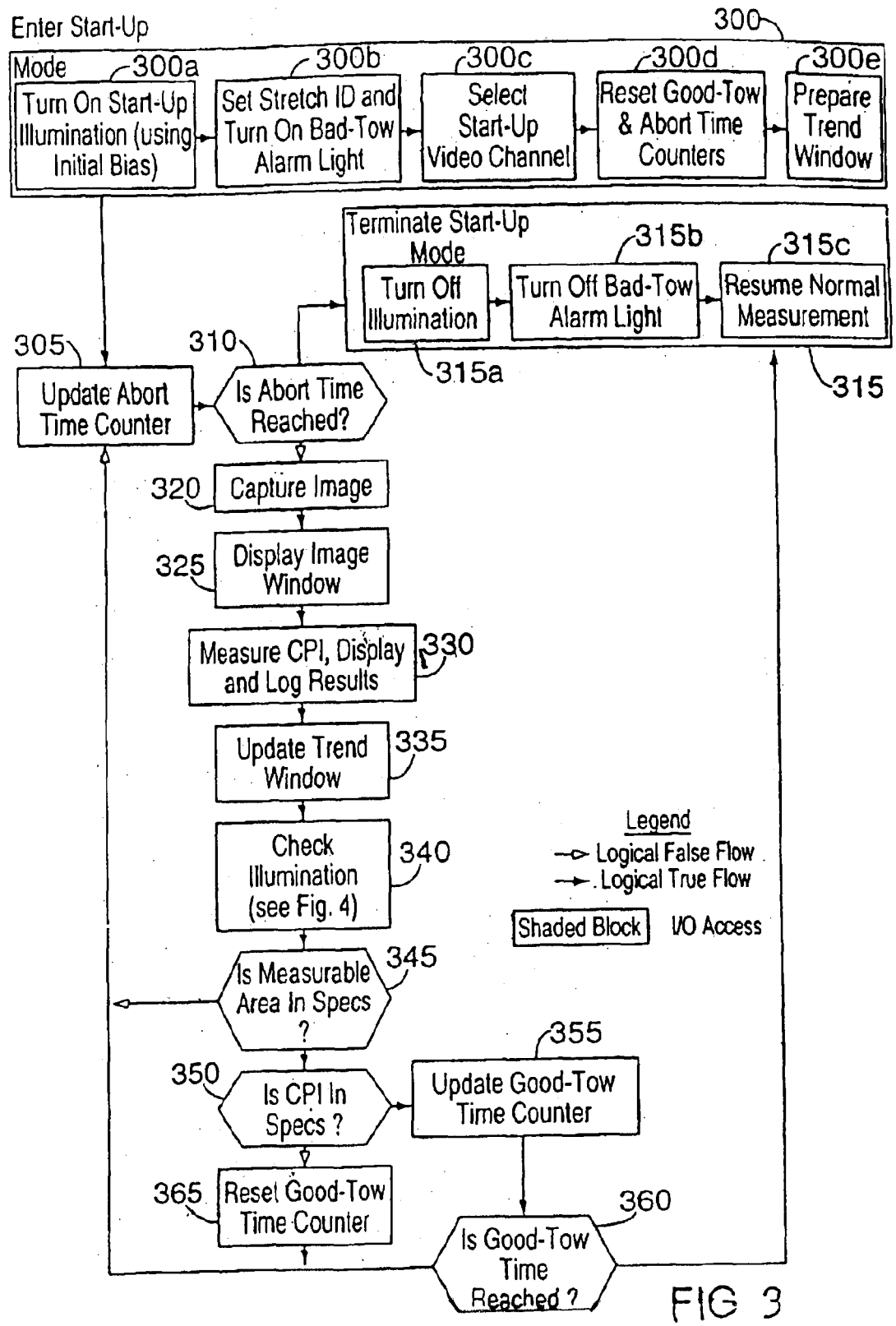
FIG. 3 is a flow chart illustration of a start-up mode process.

The start-up mode process is shown by FIG. 3. The start-up mode process is particularly advantageous when used with batch-type fiber processing, i.e., the staple fibers are provided in batches and are usually discontinuous after certain lengths. The fiber characteristics of the beginning portion of each batch is usually "uncharacteristic" or different than the rest of the batch. This is mostly due to loose ends from cutting and other deformities. The uncharacteristic beginning portions are usually cut and discarded.

The start-up mode is used to monitor the beginning portions of each batch and to alert the operator when the crimped tow reaches the "characteristic" portion of the batch, upon which the operator cuts and discards the beginning "uncharacteristic" portion. The start-up process reduces wastage due to unnecessarily discarding too long of a beginning portion and provides more uniform characteristics in each batch. The start-up mode also prevents the possible corruption of data from preventing the inclusion of measurements of the crimp characteristics of the beginning of the crimped tow with the main portion of the tow. The start-up mode activates an alarm when the good-tow is positioned in direct view of at least one camera 18 set-up for imaging the width of the moving crimped tow.

Referring to FIG. 3, the crimp measurement system is activated by turning on the contiguous light source (300a); setting the stretch line identification and turning on the bad-tow alarm light (300b) to signify the start of a batch; selecting a start-up video channel (300c) which may be a separate camera specifically situated to capture start-up images; setting the good-tow and aborting the time counters (300d); and preparing the trend window (300e).

An abort time counter is used to set a time within which to complete the start-up process. The counter is updated (305) and it is checked to determine if it has reached the pre-set abort time (310). Upon reaching the abort time, the start-up mode is terminated. The illumination is turned off (315a), the bad-tow alarm light is turned off (315b), and normal measurement is resumed (315c).

Within the abort time, images of the moving crimped tow are acquired using the start-up camera (320). The acquired images are displayed on the screen (325). The crimp per inch (CPI) parameter is measured and recorded (330), and the trend window is updated (335).

The illumination is checked by computer 10 to determine if the average image intensity is within the specifications (340). If the illumination does not meet the operator specifications, it is adjusted by increasing or decreasing the voltage to the continuous light source to increase or decrease the image intensity (405). If the voltage to the light source is exceeded (410), a system alarm is checked (415) and an alarm is activated in the following steps. An alarm/event message is displayed on the computer screen (420) for indicating to the operator of illumination or other system problems. A screen depicting an alarm/event message window is shown by FIG. 13.

A system alarm light may be turned on (430) if a system alarm I/O has been enabled as determined by step (425). The system alarm I/O is enabled through the system setting display depicted by FIG. 7d.

If the illumination does meet the operator specifications, the process returns to step 345 of FIG. 3. In step 345 the software checks to determine whether the measured area of the crimped tow is within the operator specifications. If not, the process returns to step 305 and the abort-time counter is updated. If in step 345 the software determines that the measured area of the crimped tow is within the operator specifications, the uncharacteristic beginning portion of the tow has likely moved through the system.

In step 350, stored program 11 checks to determine whether the CPI parameter of the crimped tow is within the operator specifications. If the CPI parameter is within the operator specifications, the good-tow counter is updated (355). The good-tow counter is checked to determine whether the good-tow count has been reached (360). If the good-tow counter has reached the good-tow count, the process returns to step 315 to terminate the start-up mode feature. The start-up mode feature is terminated by turning off the illumination (315a); turning off the bad-tow alarm light to indicate to the operator that the good-tow has been reached (315b); and resuming with normal crimp character- istics measurements (315c).

If in step 350 the CPI parameter is not within the operator specifications, the good-tow counter is reset (365) and the start-up process returns to step 305 where the abort time counter is updated. Similarly, if the good-tow count has not been reached, the process returns to step 305. The start-up process continues until the CPI parameter in step 350 is determined to be within the operator specifications and the good-tow count has been reached in step 360.

Figure 5:
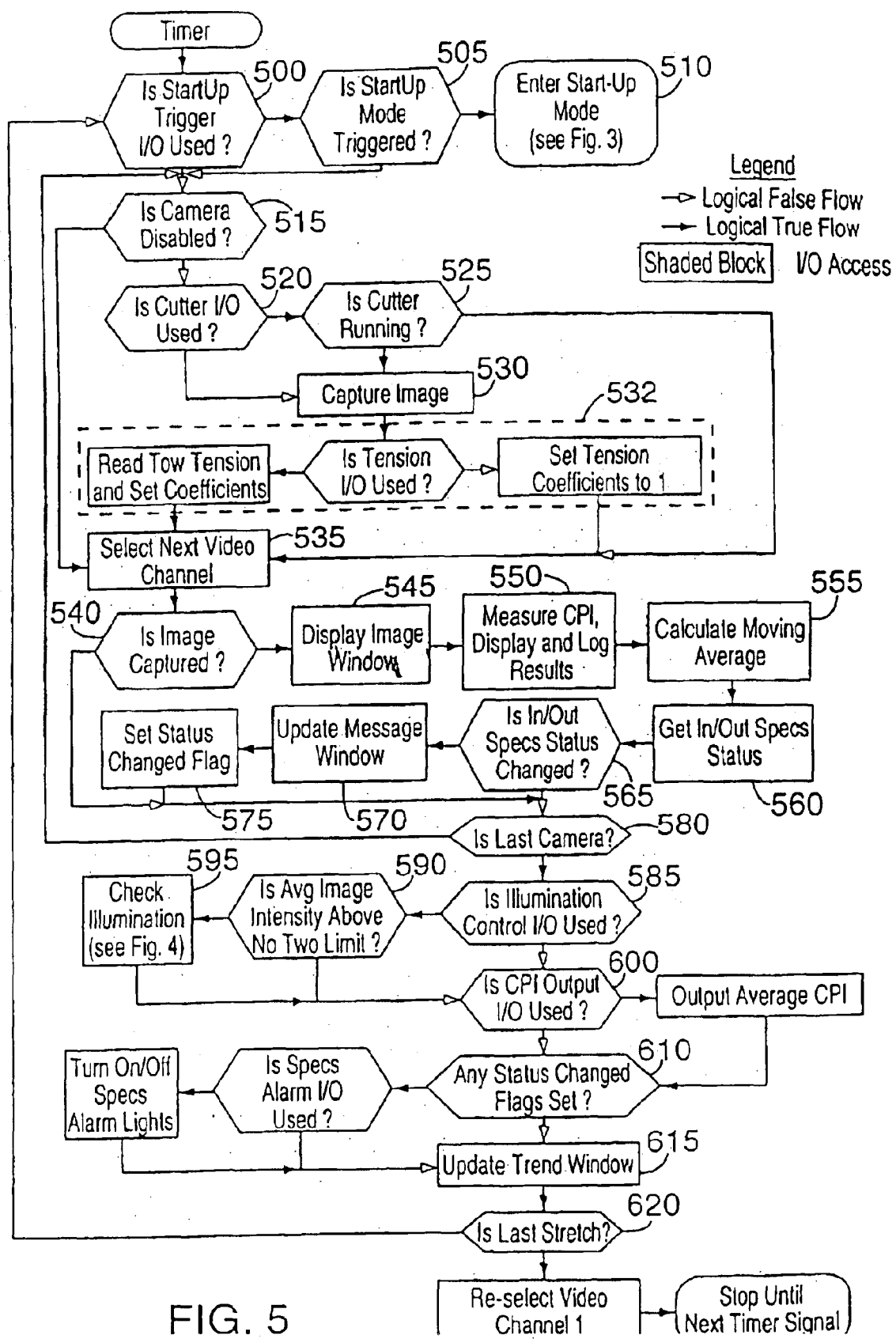
FIG. 5 is a flow chart illustration representative of a "normal crimp measurement" method.

The interaction between the software, the hardware components, and the status checks during the normal mea- surement mode is illustrated by the flow chart of FIG. 5. Steps 500 and 505 determine whether the start-up trigger has been triggered in order to toggle over to the start-up process mode depicted by the flow chart of FIG. 3. If the start-up trigger has been triggered, such as in the case of batch-type processing, normal measurement is postponed and the sys- tem proceeds with the start-up process.

In normal measurement mode, computer 10 and associ- ated program 11 determine whether camera 18 is enabled to acquire images of the moving crimped tow. The system preferably uses three cameras positioned across the width of the moving crimped tow for imaging the entire width. If one of the three cameras is disabled or has malfunctioned, measurements may continue with the other cameras. According to a preferred embodiment of the invention, three different tow stretch lines can be running at the same time with three cameras positioned across the width of each tow.

The number of tow stretch lines to be measured in the automatic operating mode is set by the setting display depicted by FIG. 6b. Stored program 11 checks the cameras 18 and the cutter before selected images are acquired. For example, when a camera 18 is enabled (515), and the cutter I/O is not enabled or the cutter is running (steps 520 and 525), an image is acquired for processing from the selected camera (step 530).

It is noted that although three cameras are chosen in the present embodiment, measurements of crimp characteristics may be made with images acquired from less than three cameras. In some instances, the operator may disable one of the three cameras. For crimp measurements and for illumi- nation control, average intensity of images from all enabled cameras are used.

If in step 515 the camera is not enabled, the next video channel is selected in step 535 and an image of the moving crimped tow from the selected camera of the video channel is received by processor 10 and stored program 11 (Step 540). If the image has not been received, the process returns to step 515.

The acquired image is displayed on the image window (545); the CPI is measured, displayed and logged (550); and the moving average is calculated (555). The measured results may be compared to the operator specifications (560) and the specifications status is checked (565), the message window is updated (570) and a flag may be set to note that the specifications status has changed (575).

Figure 4:
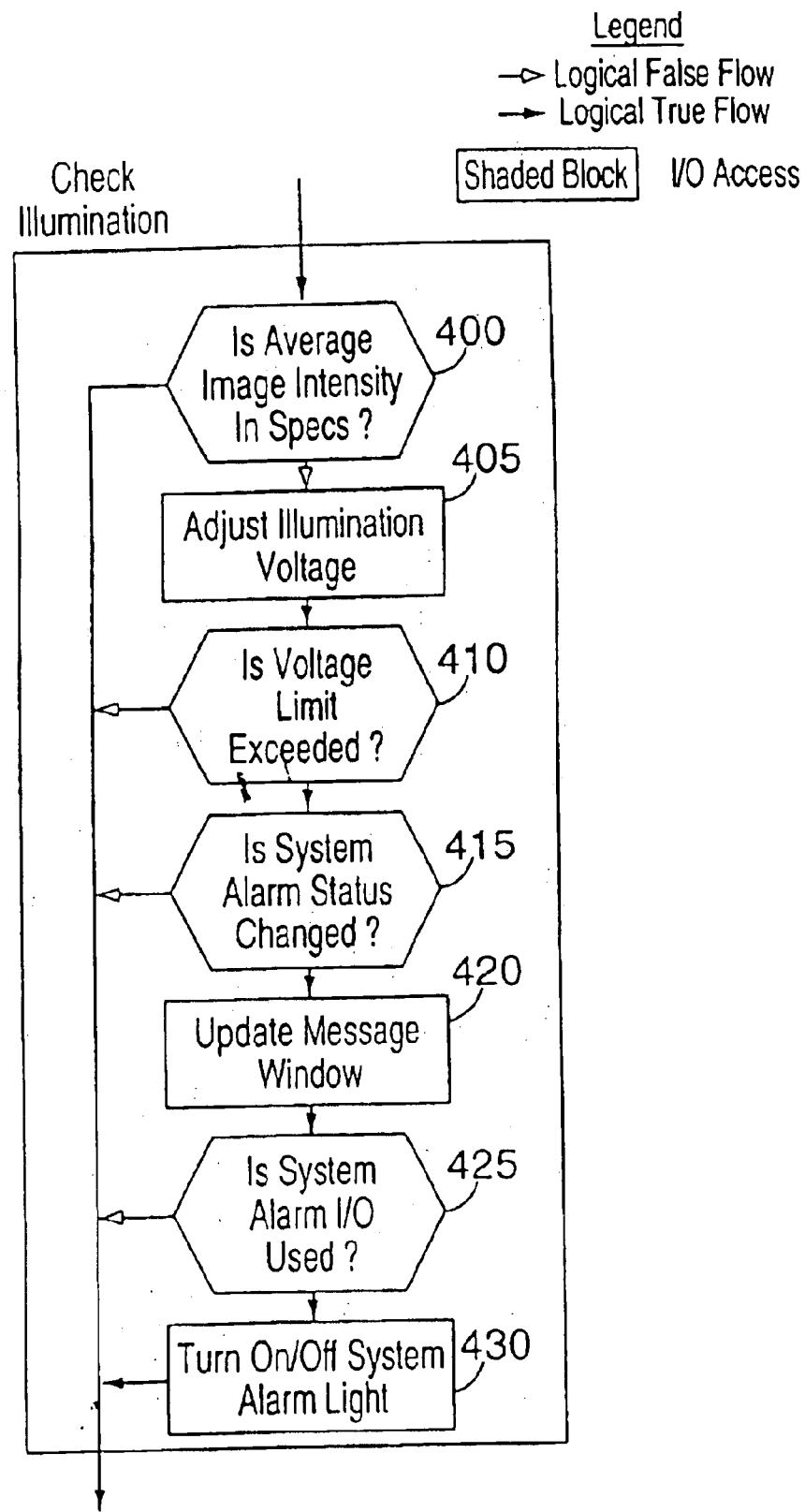
FIG. 4 is a flow chart illustration representative of a "check illumination" method.

If the specifications status has not changed or after the flag is set to note that the specifications status has changed (580), stored program 11 checks whether all enabled cameras of a tow line have been selected to forward an image of the moving crimped tow. If not, the process 515 to 580 repeats for the next camera. After all enabled cameras have for- warded an image, the process checks the illumination based on the average image intensity of the acquired images from the three cameras and if necessary, makes adjustments to the illumination control (steps 585, 590 and 595. See also FIG. 4).

The crimp measurements are also based on averages of images from the three cameras. For example, if CPI output I/O is enabled (step 605), the average CPI is output and may be displayed (step 605). In step 610 stored program 11 checks whether the measured specifications of the crimp characteristics have changed from the previous measure- ment and update the trend window accordingly in step 615 to enable the operator to view the measured on-line crimp characteristics and other measured parameters. Alarms may be used to alert the operator if the measurements are outside of pre-set specification.

The process of FIG. 5 repeats for other tow lines.

Advantageously, the use of a continuous wave (cw) light source for illuminating the moving crimped tow and pro- gressive scanning cameras obviates the need to move the light source or camera by stepper motor controls. The crimp characteristic measurements can be displayed at near real- time speed as compared to systems which use stepper motor controls. In the latter systems, the updating of the measure- ment results is much slower due to the time necessary for positioning the lighting and cameras. Consequently, system parameter adjustments are proportionately delayed in sys- tems having motorized positioning controls.

The stored program 11 further provides means for check- ing the data acquisition boards by executing diagnostic tests as indicated by the screens of FIGS. 11a–11d. These screens allow the operator, for example, to set the bit/channel positions, channel identification, and control the input and output.

It will be understood that various modifications can be made to the embodiment of the present invention herein disclosed without departing from the spirit thereof. The above description should not be construed as limiting the invention but merely as exemplifications of preferred embodiments thereof. Those skilled in the art will envision other modifications within the scope and spirit of the present invention as defined by the claims appended hereto.

What is claimed is:

1. A crimp measuring system, comprising:
   a computer, wherein the computer comprises a processor and an associated stored program and wherein the program is stored in a computer readable medium and wherein the computer and the associated stored program decomposes an acquired video image of a moving crimped tow into two non-interlaced images;

a plurality of progressive scanning video cameras, wherein the cameras are used to acquire the video image of the moving crimped tow;

a switchboard that accepts data signals from at least one of the video cameras;

an I/O interface connected to; and at least one peripheral device for I/O communication between the computer and said at least one peripheral device.

2. The crimp measuring system of claim 1, further comprising an analog video monitor connected to at least one of the progressive scanning video cameras.

3. The crimp measuring system of claim 1, wherein at least one of the progressive scanning video cameras outputs a digital data signal to the switch board.

4. The crimp measuring system of claim 1, wherein the system further comprises a frame grabber.

5. The crimp measuring system of claim 4, wherein at least one of the progressive scanning video cameras outputs a video data signal to the switch board.

6. The crimp measuring system of claim 5, wherein the video data signal is digitized by the frame grabber after the video signal reaches the switch board.

7. The crimp measuring system of claim 1, wherein the at least one peripheral device comprises a crimper controller, a tow tension sensor, a light intensity regulator, external data storage, an audio/video alarm device or a combination thereof.

8. The crimp measuring system of claim 1, wherein the processor and stored program processes the data signals by identifying crimp peaks for crimps having a value exceeding a preset threshold and calculating crimp frequencies between neighboring crimp peaks.

9. The crimp measuring system of claim 1, wherein the I/O interface comprises at least one data acquisition board.

10. The crimp measuring system of claim 9, wherein the at least one data acquisition board comprises sufficient analog and digital channels for I/O communications between the computer and the at least one peripheral device.

11. The crimp measuring system of claim 1, further comprising a light source positioned proximate to the plurality of progressive scanning video cameras.

12. The crimp measuring system of claim 11, wherein the light source illuminates a plurality of fibers in a moving crimped tow.

13. The crimp measuring system of claim 11, wherein the stored program operates the light source.

14. The crimp measuring system of claim 1, further comprising a start-up mode for processing start-up portions of a crimped tow and for signaling a normal condition upon the start-up portions satisfying a predefined criteria.

15. The crimp measuring system of claim 1, wherein the processor and the stored program divides non-interlaced image into a series of horizontal bands and for establishing an intensity profile of each of the bands by averaging pixel intensity of sequential horizontal lines within each of the bands.

16. The crimp measuring system of claim 1, wherein the processor and the stored program processes the data as minima and maxima intensity profiles wherein a maxima is labeled as a crimp peak if difference in intensity between the maxima and its two neighboring minima exceeds an operator-specified intensity threshold value.

17. The crimp measuring system of claim 1, wherein the processor and the stored program calculates distances of neighboring crimp peaks, compares the distances with operator-specified thresholds, groups the crimp peaks into one of a micro, normal or large categories, and tabulates overall crimp statistics for a non-interlaced image.

* * * * *